(12) United States Patent
von Oepen et al.

(10) Patent No.: US 10,751,485 B2
(45) Date of Patent: Aug. 25, 2020

(54) METHODS, SYSTEMS, AND DEVICES FOR SEALING AND FLUSHING A DELIVERY SYSTEM

(71) Applicant: Cephea Valve Technologies, Inc., Santa Clara, CA (US)

(72) Inventors: Randolf von Oepen, Aptos, CA (US); Sean A. McNiven, Menlo Park, CA (US); Francisco Valencia, East Palo Alto, CA (US)

(73) Assignee: Cephea Valve Technologies, Inc., Santa Clara, CA (US)

( * ) Notice: Subject to any disclaimer, the term of this patent is extended or adjusted under 35 U.S.C. 154(b) by 394 days.

(21) Appl. No.: 15/661,988

(22) Filed: Jul. 27, 2017

(65) Prior Publication Data

US 2018/0126095 A1    May 10, 2018

Related U.S. Application Data

(60) Provisional application No. 62/380,888, filed on Aug. 29, 2016, provisional application No. 62/436,926, filed on Dec. 20, 2016.

(51) Int. Cl.
*A61M 5/36* (2006.01)
*A61M 25/09* (2006.01)
(Continued)

(52) U.S. Cl.
CPC .............. *A61M 5/36* (2013.01); *A61B 90/70* (2016.02); *A61M 25/0028* (2013.01);
(Continued)

(58) Field of Classification Search
CPC .......... A61B 17/0469; A61B 2090/701; A61B 17/1285; A61B 90/70; A61B 50/30;
(Continued)

(56) References Cited

U.S. PATENT DOCUMENTS 4,728,319 A    3/1988 Masch
5,325,845 A    7/1994 Adair
(Continued)

FOREIGN PATENT DOCUMENTS

CN    102770080    11/2012
CN    103841899    6/2014
(Continued)

OTHER PUBLICATIONS

English Translation of JP2003062072, Kakizaki Takami, Mar. 4, 2003, pp. 1-20 (attached as NPL15661988_JP2003062072_EnglishTranslation.pdf) (Year: 2003).*

*Primary Examiner* — Navin Natnithithadha
*Assistant Examiner* — Sunita Reddy
(74) *Attorney, Agent, or Firm* — Workman Nydegger

(57) ABSTRACT

A method for sealing and flushing a delivery member includes sealing one or more lumens and flushing air from the one or more lumens. An interventional device delivery system includes a handle assembly and a delivery member. The handle assembly includes a catheter holder with a passageway therethrough. A flush block is associated with the catheter holder and has a flush port and a flush chamber. The delivery member is associated with the handle assembly and includes a plurality of catheters. At least one of the catheters has a proximal end disposed within the passageway in the catheter holder and is in fluid communication with the flush chamber.

13 Claims, 6 Drawing Sheets

(51) Int. Cl.
*A61M 25/00* (2006.01)
*A61M 39/22* (2006.01)
*A61B 90/70* (2016.01)
*A61B 50/30* (2016.01)
*A61F 2/95* (2013.01)
*A61B 17/04* (2006.01)
*A61B 17/128* (2006.01)
*A61F 2/24* (2006.01)
*A61M 25/01* (2006.01)

(52) U.S. Cl.
CPC .... *A61M 25/09041* (2013.01); *A61M 39/225* (2013.01); *A61B 17/0469* (2013.01); *A61B 17/1285* (2013.01); *A61B 50/30* (2016.02); *A61B 2090/701* (2016.02); *A61F 2/2436* (2013.01); *A61F 2/2466* (2013.01); *A61F 2002/9517* (2013.01); *A61M 25/0136* (2013.01); *A61M 25/0147* (2013.01); *A61M 2025/0004* (2013.01); *A61M 2025/0018* (2013.01); *A61M 2209/04* (2013.01)

(58) Field of Classification Search
CPC ........ A61M 2025/0004; A61M 39/225; A61M 25/09041; A61M 25/0147; A61M 2209/04; A61M 25/0028; A61M 5/36; A61M 25/0136; A61M 2025/0018; A61F 2/2466; A61F 2/2436; A61F 2002/9517
USPC .................................. 128/897–899
See application file for complete search history.

(56) References Cited

U.S. PATENT DOCUMENTS

| | | | |
|---|---|---|---|
| 5,769,812 A | 6/1998 | Stevens et al. | |
| 5,855,601 A | 1/1999 | Bessler et al. | |
| 6,090,118 A | 7/2000 | McGuckin, Jr. | |
| 6,517,550 B1 | 2/2003 | Konya et al. | |
| 7,666,204 B2 | 2/2010 | Thornton et al. | |
| 7,736,388 B2 | 6/2010 | Goldfarb et al. | |
| 7,837,727 B2 | 11/2010 | Goetz et al. | |
| 7,988,724 B2 | 8/2011 | Salahieh et al. | |
| 8,157,852 B2 | 4/2012 | Bloom et al. | |
| 8,523,881 B2 | 9/2013 | Cabiri et al. | |
| 8,911,455 B2 | 12/2014 | Quadri et al. | |
| 8,926,588 B2 | 1/2015 | Berthiaume et al. | |
| 9,339,378 B2 | 5/2016 | Quadri et al. | |
| 9,370,423 B2 | 6/2016 | Ryan | |
| 9,393,112 B2 | 7/2016 | Tuval et al. | |
| 9,399,112 B2 | 7/2016 | Shevgoor et al. | |
| 10,376,673 B2 | 8/2019 | Van Hoven et al. | |
| 2001/0041865 A1* | 11/2001 | Delaney | A61B 5/14539 604/102.01 |
| 2002/0013547 A1 | 1/2002 | Paskar | |
| 2003/0199916 A1* | 10/2003 | Yee | A61F 2/95 606/198 |
| 2004/0049207 A1 | 3/2004 | Goldfarb et al. | |
| 2004/0147826 A1 | 7/2004 | Peterson | |
| 2005/0059931 A1* | 3/2005 | Garrison | A61M 25/10 604/101.04 |
| 2005/0085903 A1 | 4/2005 | Lau | |
| 2005/0137695 A1 | 6/2005 | Salahieh et al. | |
| 2005/0283231 A1 | 11/2005 | Haug et al. | |
| 2005/0277876 A1 | 12/2005 | Hayden | |
| 2006/0135961 A1 | 6/2006 | Rosenman et al. | |
| 2007/0010782 A1* | 1/2007 | Doty | A61B 17/12045 604/20 |
| 2007/0260225 A1 | 11/2007 | Sakakine et al. | |
| 2009/0099554 A1 | 4/2009 | Forster et al. | |
| 2009/0163934 A1 | 6/2009 | Raschdorf, Jr. et al. | |
| 2009/0234176 A1* | 9/2009 | Lebovic | A61N 5/1016 600/6 |
| 2009/0240326 A1 | 9/2009 | Wilson et al. | |
| 2009/0281619 A1 | 11/2009 | Le et al. | |
| 2010/0217261 A1 | 8/2010 | Watson | |
| 2010/0331776 A1 | 12/2010 | Salahieh et al. | |
| 2011/0112630 A1 | 5/2011 | Groothuis et al. | |
| 2012/0022640 A1 | 1/2012 | Gross et al. | |
| 2012/0078029 A1* | 3/2012 | Subramanian | A61M 25/0017 600/3 |
| 2012/0172915 A1 | 7/2012 | Fifer et al. | |
| 2012/0330408 A1 | 12/2012 | Hillukka et al. | |
| 2013/0066342 A1 | 3/2013 | Dell et al. | |
| 2014/0114307 A1* | 4/2014 | Moisa | A61B 18/1492 606/41 |
| 2015/0112318 A1* | 4/2015 | Crisostomo | A61B 17/00 606/1 |
| 2015/0112430 A1 | 4/2015 | Creaven et al. | |
| 2015/0314111 A1* | 11/2015 | Solar | A61M 25/0026 604/509 |
| 2016/0045311 A1 | 2/2016 | McCann et al. | |
| 2018/0092744 A1 | 4/2018 | von Oepen et al. | |

FOREIGN PATENT DOCUMENTS

| | | |
|---|---|---|
| EP | 2537487 | 12/2012 |
| JP | 2003062072 | 3/2003 |
| JP | 2006528911 | 12/2006 |
| WO | WO 2007044285 | 4/2007 |
| WO | WO 2007136829 | 11/2007 |
| WO | WO 2008103722 | 8/2008 |
| WO | WO 2010024801 | 3/2010 |
| WO | WO 2010121076 | 10/2010 |
| WO | WO 2014121280 | 8/2014 |
| WO | WO 2014128705 | 8/2014 |
| WO | WO 2016144708 | 9/2016 |
| WO | WO 2016150806 | 9/2016 |
| WO | WO 2018044450 | 3/2018 |

\* cited by examiner

METHODS, SYSTEMS, AND DEVICES FOR SEALING AND FLUSHING A DELIVERY SYSTEM

CROSS-REFERENCE TO RELATED APPLICATIONS

This application claims the benefit of and priority to: U.S. Provisional Patent Application Ser. No. 62/380,888, filed Aug. 29, 2016 and titled "Methods, Systems, and Devices for Sealing and Flushing a Delivery System"; and U.S. Provisional Patent Application Ser. No. 62/436,926, filed Dec. 20, 2016 and titled "Methods, Systems, and Devices for Sealing and Flushing a Delivery System," the disclosures of which are incorporated herein by references in their entireties.

BACKGROUND OF THE DISCLOSURE

1. The Field of the Disclosure

The present disclosure generally relates to methods, systems, and devices for sealing and flushing a delivery system or delivery catheter.

2. The Relevant Technology

Intravascular medical procedures allow the performance of therapeutic treatments in a variety of locations within a patient's body while requiring only relatively small access incisions. An intravascular procedure may, for example, eliminate the need for open-heart surgery, reducing risks, costs, and time associated with an open-heart procedure. The intravascular procedure also enables faster recovery times with lower associated costs and risks of complication. An example of an intravascular procedure that significantly reduces procedure and recovery time and cost over conventional open surgery is a heart valve replacement or repair procedure. An artificial valve is guided to the heart through the patient's vasculature. For example, a catheter is inserted into the patient's vasculature and directed to the inferior vena cava. The catheter is then urged through the inferior vena cava toward the heart by applying force longitudinally to the catheter. Upon entering the heart from the inferior vena cava, the catheter enters the right atrium. The distal end of the catheter may be deflected by one or more deflecting mechanisms, which can be achieved by tension cable, or other mechanisms positioned inside the catheter. Precise control of the distal end of the catheter allows for more reliable and faster positioning of a medical device and/or implant and other improvements in the procedures.

An intravascularly delivered device needs to be placed precisely to ensure a correct positioning of the medical device, which is essential for its functionality, as the device may be difficult to reposition after the device is fully deployed from the delivery system. Additionally, the ability to recapture a partially deployed device is desirable in the event that the distal end of the catheter moves relative to the target location and compromises the precise positioning of the device.

The expansion and/or recapture of the device requires the collapse of one or more movable or deformable portions of the device. The one or more movable or deformable portions expand and/or collapse toward the longitudinal axis of a sheath during longitudinal movement of the sheath over the transverse exterior of the device. Proximal movement of the sheath relative to the device allows the device to expand beyond a diameter of the sheath. Distal movement of the sheath relative to the device constrains the device in the tip of the sheath. More rigid and/or robust devices with a high outwards force require a stiffer sheath and/or greater longitudinal forces to move the sheath relative to the device. Increasing the stiffness of the sheath is undesirable during intravascular procedures since a stiff device might not be able to be delivered through a tortuous anatomy.

BRIEF SUMMARY OF THE DISCLOSURE

Provided are sealing and flushing methods, systems, and devices to ensure that no air or unwanted fluid is trapped in a delivery device when it will be delivered through the vasculature of a patient. For instance, one embodiment includes a method for sealing and flushing a delivery member. The method includes sealing one or more lumens of the delivery member and flushing a fluid from the one or more lumens. In some embodiments, the flushing is done with $CO_2$.

According to another embodiment, a method for sealing and flushing a delivery member includes sealing (i) a guide wire lumen, (ii) at least one suture lumen of a suture catheter which receives the guide wire lumen, (iii) a delivery catheter disposed about both the suture catheter and the guide wire lumen, and (iv) an outer sheath disposed about the delivery catheter. The method also includes flushing a fluid from the guide wire lumen, the at least one suture lumen, a lumen associated with the delivery catheter, and a lumen of the outer sheath.

According to another embodiment, an interventional device delivery system includes a handle assembly and a delivery member. The handle assembly includes a catheter holder with a passageway therethrough. A flush block is associated with the catheter holder and has a flush port and a flush chamber. The delivery member is associated with the handle assembly and includes a plurality of catheters. At least one of the catheters has a proximal end disposed within the passageway in the catheter holder and is in fluid communication with the flush chamber.

Additional features and advantages will be set forth in part in the description that follows, and in part will be obvious from the description, or may be learned by practice of the embodiments disclosed herein. The objects and advantages of the embodiments disclosed herein will be realized and attained by means of the elements and combinations particularly pointed out in the appended claims. It is to be understood that both the foregoing brief summary and the following detailed description are exemplary and explanatory only and are not restrictive of the embodiments disclosed herein or as claimed.

BRIEF DESCRIPTION OF THE DRAWINGS

In order to describe various features and concepts of the present disclosure, a more particular description of certain subject matter will be rendered by reference to specific embodiments which are illustrated in the appended drawings. Understanding that these figures depict just some example embodiments and are not to be considered to be limiting in scope, various embodiments will be described and explained with additional specificity and detail through the use of the accompanying drawings in which:

FIG. 2-1 illustrates a cross-section of the delivery member, showing various nested components of the delivery member, including an outer sheath, a steering catheter, a delivery catheter, a suture catheter, and a guidewire tube;

FIG. 2-2 illustrates another cross-section of the delivery member;

FIG. 3-1 illustrates a cross-section of a catheter holder that is usable with the handle assembly of FIG. 1;

DETAILED DESCRIPTION

The present disclosure is directed to devices, systems, and methods for delivering, positioning, and deploying interventional devices, such as intravascular devices, replacement heart valve devices, valve repair devices, annuloplasty devices, clip devices, and other interventional devices not necessarily configured as a replacement valve. More specifically, the present disclosure is directed to methods, systems, and devices for sealing and flushing a delivery member to ensure that no air or unwanted fluid is trapped in the delivery member when it will be delivered through the vasculature of a patient.

As discussed herein, the devices and systems can include a multi-layered elongated delivery member (also referred to herein as simply the elongated member or the delivery member). The delivery member can include a plurality of catheter and/or hypotube members which provide different functionality during operation of the delivery system to enable effective delivery and deployment of the interventional devices. With use a delivery member with multiple components, sufficient flushing of the delivery member is to occur before it can be inserted into the vasculature of the human anatomy. As discussed herein, the disclosed delivery systems and devices enable flushing of the various delivery member elements.

Figure 1:
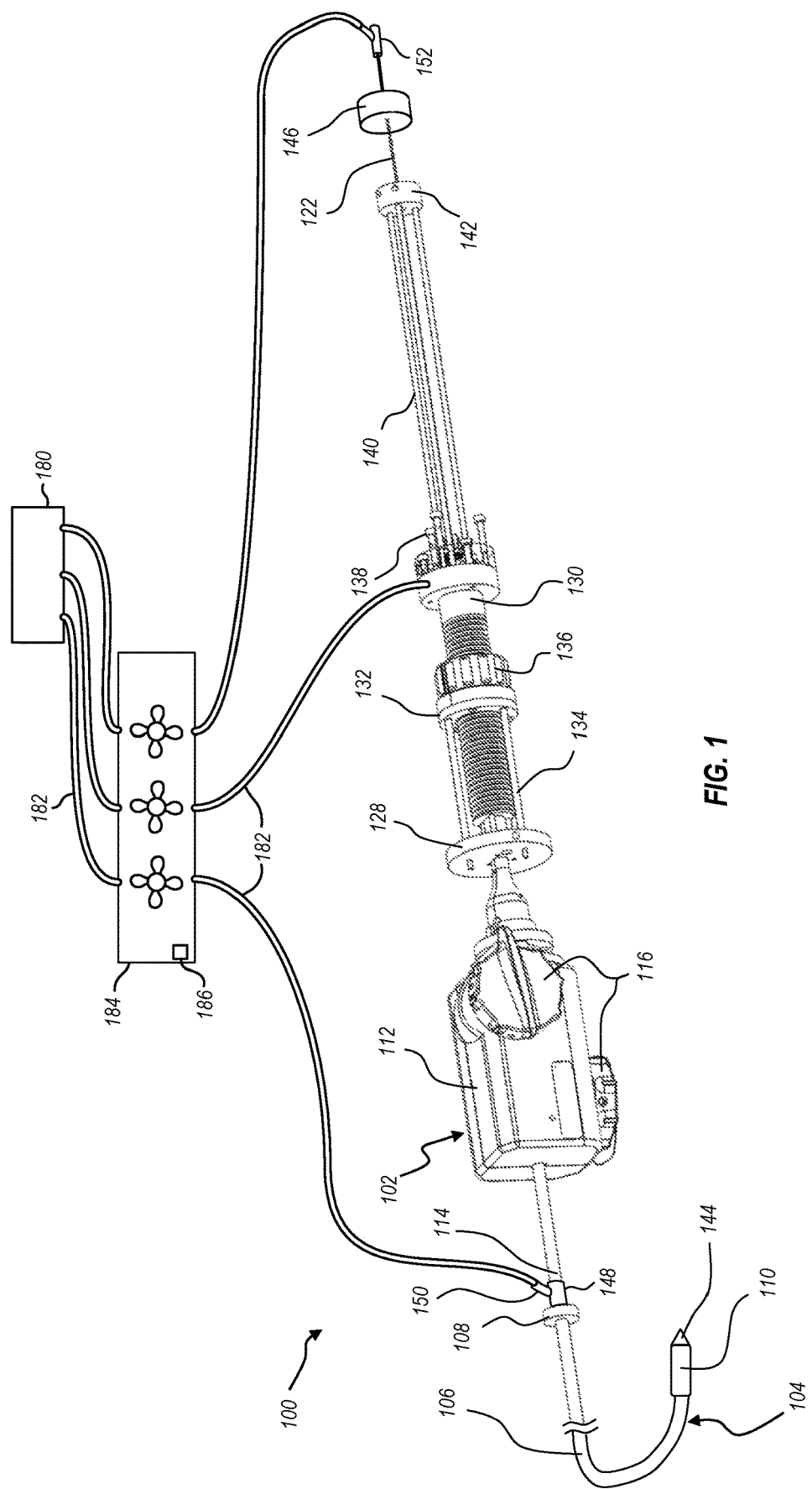
FIG. 1 illustrates a delivery system configured for delivering, positioning, and deploying an interventional device, the delivery system including a handle assembly coupled to an delivery member.

With reference to the drawings, FIG. 1 illustrates an embodiment of a delivery system 100. As shown, the delivery system 100 includes a handle assembly 102 and an elongated delivery member 104. The delivery member 104 is coupled to the handle assembly 102 and extends distally from the handle assembly 102. The delivery member 104 includes a plurality of catheter and/or hypotube members which provide different functionality during operation of the delivery system 100 to enable effective delivery and deployment of an interventional device.

The proximal end of an outer sheath 106 (also referred to herein as delivery sheath 106) is coupled to an end ring 108, and the outer sheath 106 extends to a distal end where it is coupled to an interventional device cover 110. The interventional device cover 110 functions to house an intervention device during delivery of the interventional device to the targeted site. A steering catheter handle 112 is disposed proximal of the end ring 108. The proximal end of a steering catheter 114 is coupled to the steering catheter handle 112, and the steering catheter 114 extends distally from the steering catheter handle 112 into the outer sheath 106. The steering catheter handle 112 includes one or more controls 116 which are operatively coupled to the steering catheter 114 so that manipulation of the controls 116 adjusts the curvature of the steering catheter 114. Because the steering catheter 114 is nested within the outer sheath 106, curving of the steering catheter 114 causes corresponding curving/steering in the outer sheath 106. The illustrated embodiment of the delivery member 104 includes additional components which are not visible in the view of FIG. 1 but may be seen in the cross-sectional views of FIGS. 2-1 and 2-2.

Figures 1, 2:
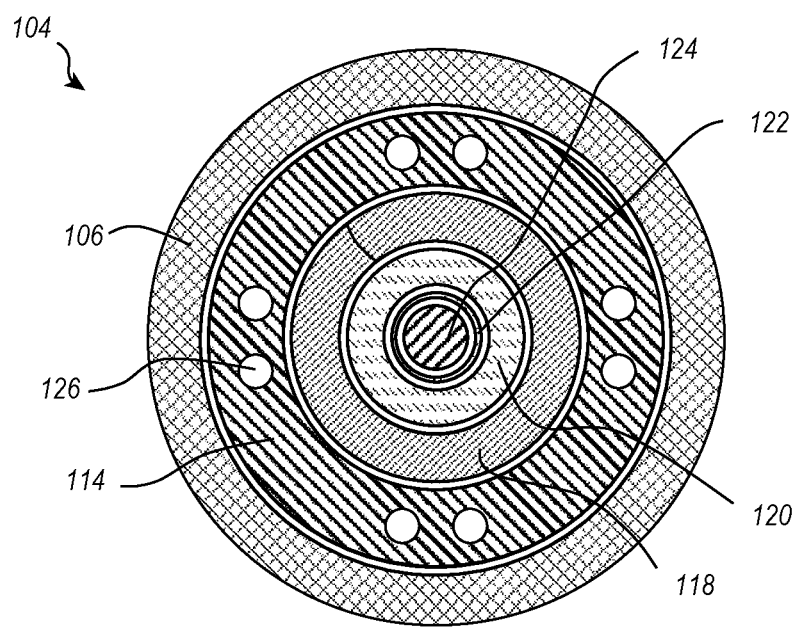
Figure 2:
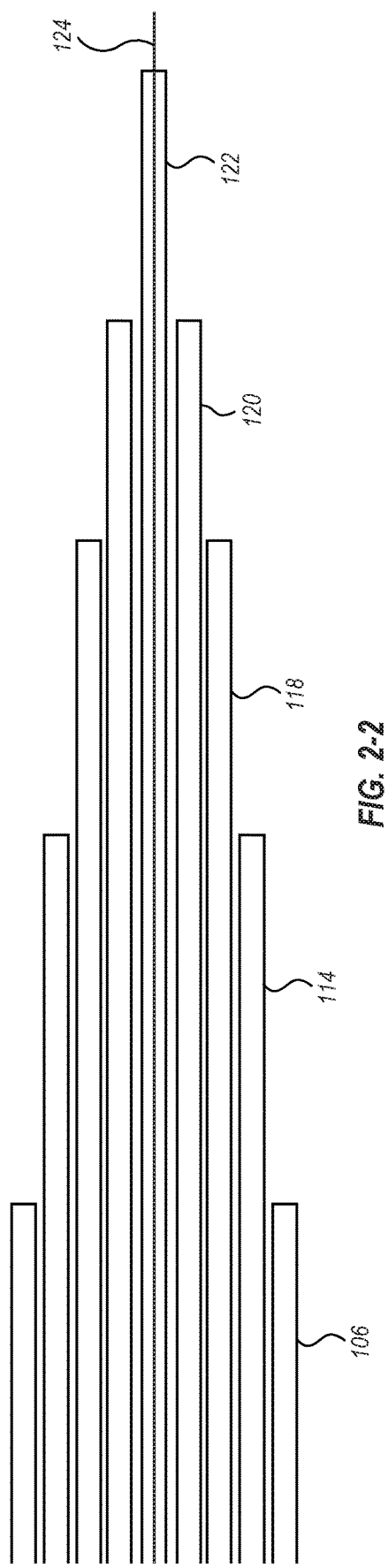

FIG. 2-1 illustrates a cross-sectional view of the delivery member 104 transverse to a longitudinal axis thereof and FIG. 2-2 is a cross-sectional view parallel to a longitudinal axis thereof. As shown, the steering catheter 114 is disposed within the outer sheath 106. A delivery catheter 118 is disposed within the steering catheter 114. A suture catheter 120 is disposed within the delivery catheter 118, and a guidewire tube 122 is disposed within the suture catheter 120. The guidewire tube 122 is configured for receiving a guidewire 124.

Although the particular nested configuration shown in FIGS. 2-1 and 2-2 represent one example embodiment, alternative embodiments may include a different concentric arrangement of constituent parts. For example, some embodiments may configure the outermost member with steering functionality, some embodiments may include more than one catheter with steering functionality, and some embodiments may trade the radial positions of the suture catheter 120 and delivery catheter 118, etcetera. Furthermore, while the illustrated embodiment of a delivery member 104 includes six coaxial members, it will be understood that more or fewer members can be used. Additionally, the members of the delivery member need not be coaxial, but can be at least partially received within one another and can be radially offset.

As shown in FIG. 2-1, the steering catheter 114 includes a plurality of lumens 126 extending through the length of the steering catheter 114. The lumens 126 may be configured for receiving tension cables which extend between the controls 116 and the distal end of the steering catheter 114. One or more tension cables may additionally or alternatively be coupled to intermediate sections of the steering catheter 114. Manipulation of the controls 116 can adjust tension in the tension cables to increase or decrease curvature of the steering catheter 114 at various positions. Although the controls 116 are shown in FIG. 1 as knobs, alternative embodiments may additionally or alternatively include one or more buttons, sliders, ratcheting mechanisms, or other suitable controls capable of adjusting tension to provide steering. Illustrative structures that can be used as part of the steering catheter handle 112 and or steering catheter 114 are described in U.S. Pat. No. 7,736,388, the disclosure of which is incorporated herein by this reference.

Referring again to FIG. 1, a delivery catheter holder 128 is disposed proximal of the steering catheter handle 112. Although not visible in the view of FIG. 1, the proximal end of the delivery catheter 118 may be coupled to the delivery catheter holder 128. The delivery catheter 118 extends distally away from the delivery catheter holder 128 and into the steering catheter 114. A suture catheter holder 130 is disposed proximal of the delivery catheter holder 128. Although not visible in FIG. 1, the proximal end of the suture catheter 120 may be coupled to the suture catheter holder 130. The suture catheter 120 extends distally away from the suture catheter holder 130 and into the delivery catheter 118.

An alignment ring 132 and alignment rods 134 provide structural support for maintaining proper alignment of the delivery catheter holder 128 and suture catheter holder 130, which thereby functions to maintain coaxial alignment of the delivery catheter 118 and suture catheter 120. A suture catheter control 136 is coupled to the alignment ring 132 and is operatively coupled to the suture catheter holder 130. Manipulation of the suture catheter control 136 adjusts the relative positioning of the delivery catheter holder 128 and suture catheter holder 130. In the illustrated embodiment, the suture catheter control 136 operates through threaded engagement with the suture catheter holder 130, such that rotation of the suture catheter control 136 translates the suture catheter holder 130 relative to the suture catheter control 136 and therefore relative to the delivery catheter holder 128. Alternative embodiments may additionally or alternatively include one or more of a slider and rail assembly, a ratcheting mechanism, or other suitable means of linear adjustment.

The illustrated suture catheter holder 130 also includes a set of tensioner posts 138. In some embodiments, sutures may extend from the distal end of the suture catheter 120 to the tensioner posts 138. The sutures may be wrapped around respective tensioner posts 138 such that screwing/unscrewing of the tensioner posts 138 adjusts tension of the coupled sutures. In other embodiments, the sutures are attached to a distal connection ring rather than extend throughout the length of the catheter. In such an embodiment, the tensioner posts 138 may be omitted.

A second set of alignment rods 140 extend proximally from the suture catheter holder 130 and connect to an alignment cap 142. The guidewire tube 122 extends distally through the alignment cap 142 and into the suture catheter 120 at the suture catheter holder 130. The guidewire tube 122 extends to the distal end of the delivery member 104 where it is attached to a distal tip 144.

The guidewire tube 122 may be selectively translatable relative to the suture catheter holder 130, so that the guidewire tube 122 and distal tip 144 may be linearly translated relative to the suture catheter 120. In the illustrated embodiment, the guidewire tube 122 is coupled to a guidewire tube handle 146. The guidewire tube 122 and guidewire tube handle 146 may be selectively locked relative to the suture catheter holder 130, such as through a set screw, clamp, or other selective fastener. For example, such a fastening structure may be associated with the alignment cap 142.

When the guidewire tube 122 is linearly locked to the alignment cap 142, movement of the delivery catheter holder 130 will translate to the alignment cap 142 and to the guidewire tube 122. The distal tip 144 and suture catheter 120 will thus move together. When unlocked, the guidewire tube 122 (and likewise the distal tip 144) may be moved relative to the suture catheter 120.

With use of a delivery member with multiple components, such as delivery member 104, sufficient flushing of the delivery member is to occur before insertion into the vasculature of the human anatomy. The flushing of some of the delivery member components can be achieved with standard hemostasis valves. For instance, as shown in FIG. 1, a hemostasis valve 148 is disposed about the steering catheter 114 and connected to the proximal end of the outer sheath 106. The hemostasis valve 148 includes a flush port 150 to which a pressurized line may be connected (e.g., with a luer connection) to introduce a flushing fluid or gas between the steering catheter 114 and the outer sheath 106. Similarly, a hemostasis valve 152 can be connected to the proximal end of the guidewire tube 122 to enable connection of a pressurized line to flush the guidewire tube 122.

To flush the other components of the delivery member 104, the delivery system 100 may provide one or more additional access points where pressurized line(s) may be connected to introduce a flush fluid or gas into the components of the delivery member 104. The pathways for some of the lumens or the spaces between adjacent components of the deliver member 104 may be especially challenging since the lumens or spaces have dimensions as small as 0.002 inches. Some of these lumens or spaces are used for sutures and wires that will be connected to an intravascular device, such as a valve or repair device, and will enable the loading of the intravascular device as well as the release. It is suggested that all lumen or spaces before they will be flushed with saline or other flushing fluids can be flushed with $CO_2$. The viscosity of a gas compared to a liquid is significantly lower and therefore it will be much easier to replace the entrapped air with a gas like $CO_2$. $CO_2$ is frequently used in medical application and especially in the peripheral vessels as a contrast medium. The gas, when in contact with blood, will dissolve quickly without causing any air emboli.

In some embodiments, the entire delivery member 104 is flushed with $CO_2$ during production and sealed in a gas tight bag or some other flexible or hard-shell container that will be filled with $CO_2$. This will guarantee that all lumens in the delivery member 104 will be filled with the inert gas and any air emboli can be eliminated. In yet other embodiments, all flush ports will be closed to ensure that the gas will stay in the lumens and spaces. Following packing in an airtight package, the delivery member 104 can be sterilized using ETO, gamma or e-beam. Before use, the delivery member 104 can optionally be flushed with saline solution or can be used directly with the $CO_2$ in the lumens or spaces of the delivery member 104.

Figure 3:
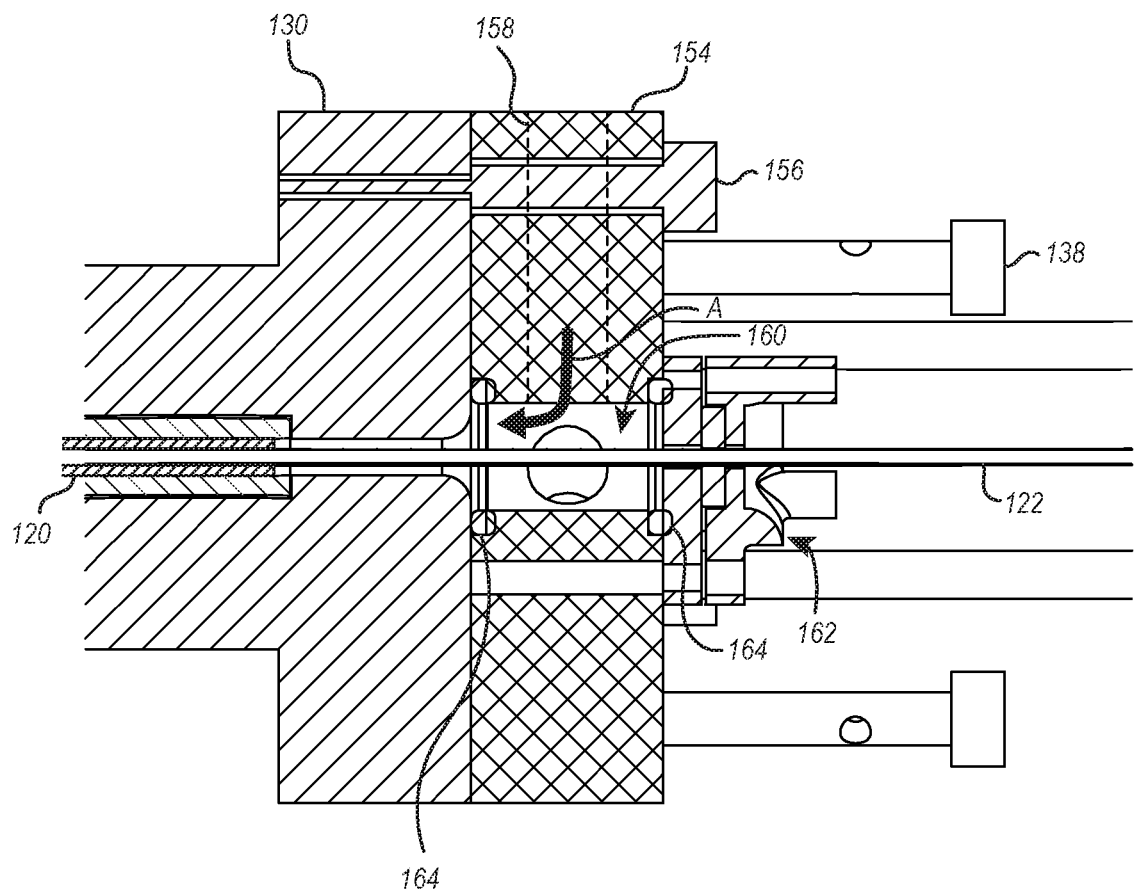
FIG. 3 illustrates a cross-section of a portion of the delivery system where a flushing fluid or gas can be introduced to flush the delivery member.
Figures 1, 3:
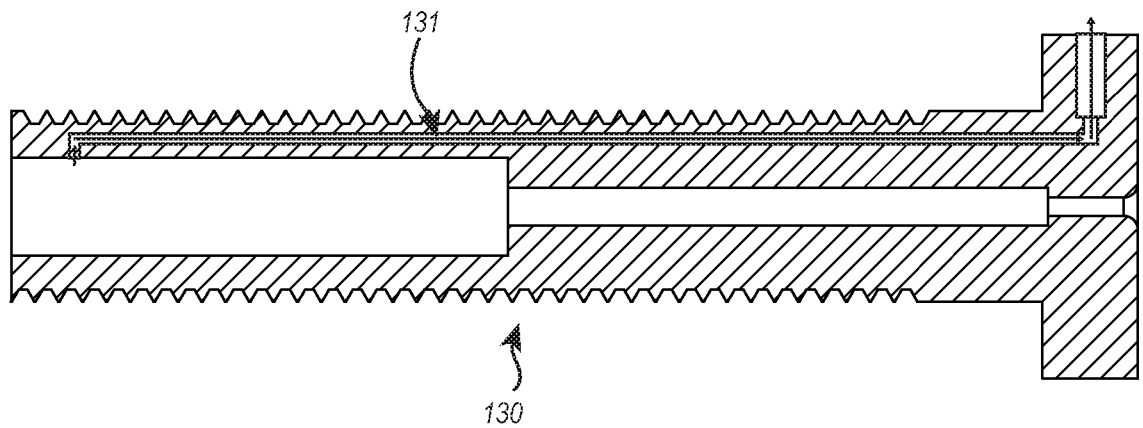

FIG. 3 illustrates one embodiment of an access point where a flushing fluid or gas can be introduced into the delivery member 104. The access point is provided at the proximal end of the suture catheter holder 130. More specifically, a flush block 154 is connected to a proximal end of the suture catheter holder 130 via one or more fasteners 156 (e.g., screws, bolts, pins, clamps, adhesives, etc.). The flush block 154 has a port 158 to which a pressurized line may be connected (e.g., via a luer connection) to introduce a flushing fluid or gas into the flush block 154.

The port 158 is in fluid communication with a flush chamber 160 within the flush block 154. The distal end of the flush chamber 160 is open to a passageway through the suture catheter holder 130, while a proximal end of the flush chamber 160 is closed off by a gasket assembly 162. The interfaces between the flush block 154 and the suture catheter holder 130 and between the flush block the 154 and the gasket assembly 162 can be sealed by one or more seals 164 disposed therebetween. As a result, a flushing fluid or gas introduced into the flush block 154 will pass through the flush chamber 160 and into the suture catheter holder 130 around the guidewire tube 122, as shown by arrow A in FIG. 3.

As the flushing fluid or gas flows into the suture catheter holder 130, the flushing fluid or gas will pass between the guidewire tube 122 and the suture catheter 120. After the cavities between the guidewire tube 122 and the suture catheter 120 and between the suture catheter 120 and the suture catheter holder 130 have been filled with the flushing fluid or gas, increased pressure (e.g., due to the decreased amount of unfilled space within the delivery member 104 and/or an increase in the pressure used to introduce that flushing fluid or gas into the device) will cause the flushing fluid or gas to pass through lumens (see FIG. 5) within the wall of the suture catheter 120.

In some embodiments, the suture catheter handle 130 may include a vent channel to allow air trapped in the suture catheter handle 130 to be released when a flushing fluid or gas is introduced. For instance, as that shown in FIG. 3-1, the suture catheter handle 130 includes a vent channel 131 that is in fluid communication with the passageway extending through the suture catheter handle 130 and an exterior of the suture catheter handle 130. In some embodiments, the vent channel 131 may be a straight channel between the interior and exterior of the suture catheter handle 130. In other embodiments, the vent channel 131 may have multiple legs, some of which extend longitudinally and some which extend transverse to the suture catheter handle 130. In still other embodiments, the vent channel 131 may include one or more valves that selectively open or close either under specified pressure differentials or through manual operation. In any event, after the flushing fluid or gas has been introduced into the suture catheter handle 130 as described above and has replaced all air trapped in the suture catheter handle 130, the vent channel 131 can be closed. Thereafter, the pressure of the flushing fluid or gas can be increased to force the flushing fluid or gas through the components of the delivery member 104.

Figure 4:
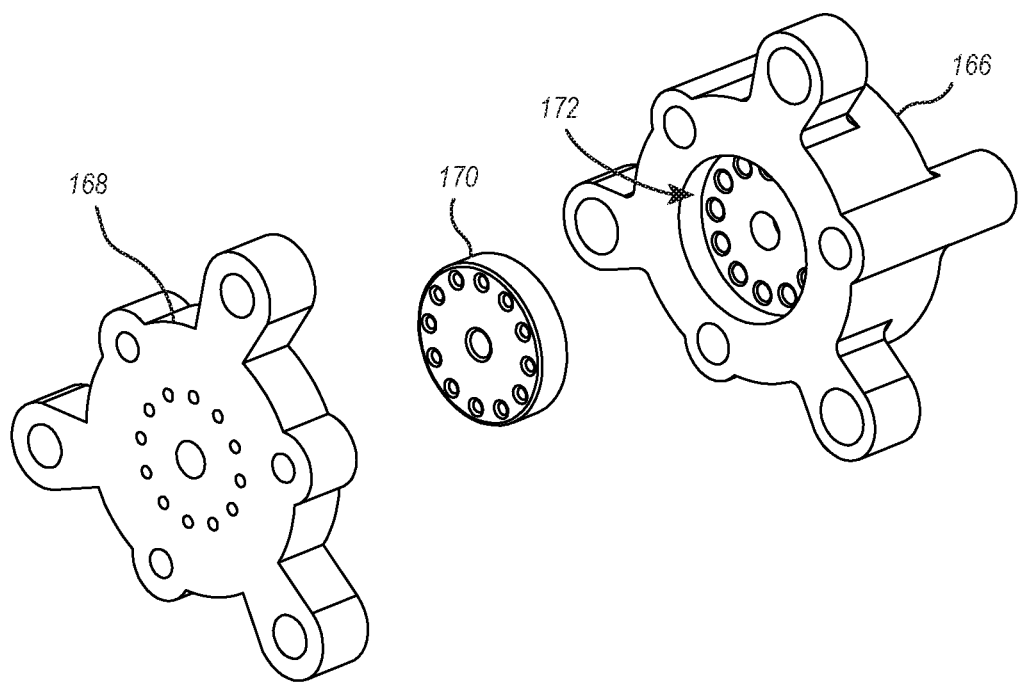
FIG. 4 illustrates an exploded view of a gasket assembly of the handle assembly of FIG. 1.

As noted, the proximal end of the flush chamber 160 is closed off by the gasket assembly 162. FIG. 4 illustrates an exploded view of the gasket assembly 162, showing a proximal plate 166, a distal plate 168, and a gasket 170 thereof. In the illustrated embodiment, the proximal plate includes a pocket or recess 172 into which a portion of the gasket 170 is received. With the gasket 170 disposed within the pocket 172, the proximal and distal plates 166, 168 can be connected together (e.g., via fasteners, screws, bolts, adhesives, clamps, etc.) as shown in FIG. 3. When the proximal and distal plates 166, 168 are connected together, the gasket 170 is compressed therebetween. The gasket 170 can be soft silicon, TPU, FEP, PFTE or any other material suitable for sealing.

Figure 5:
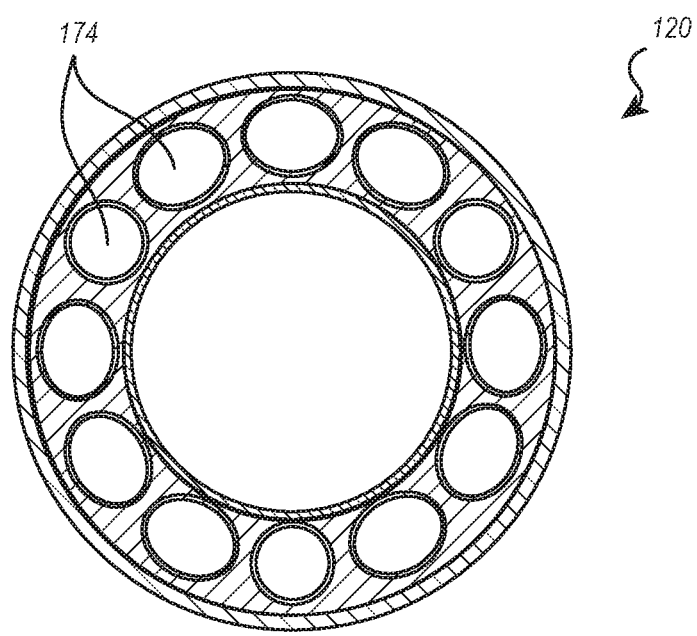
FIG. 5 illustrates a cross-section of a suture catheter of the delivery member of FIG. 1.

The interventional device can be connected to the handle assembly with sutures, wires, or other elongate structures. The sutures or wires can run through the wall of the suture catheter 120. An exemplary cross section of the suture catheter 120 is shown in FIG. 5. As can be seen, the suture catheter 120 includes a plurality of lumens 174 extending through the wall thereof in a longitudinal direction. The number of sutures or wires may correspond to the number of lumens 174 in the suture catheter 120, or vice versa. Each suture can be stitched through the gasket 170. At its proximal end, the gasket 170 can have a small chamfer to guide the needle or stiletto connected to the suture through the gasket 170. The stitching of the suture through the gasket 170 can enable a safe sealing. In some embodiments, additional lumens 174 may be provided for additional functions, such as adding a tension cable to be connected to an end ring, tension cable to be connected to the outer sheath 106, electrical cable to be connected to a circuit board to terminate suture by shorting a circuit and creating heat, or other functions.

Figure 6:
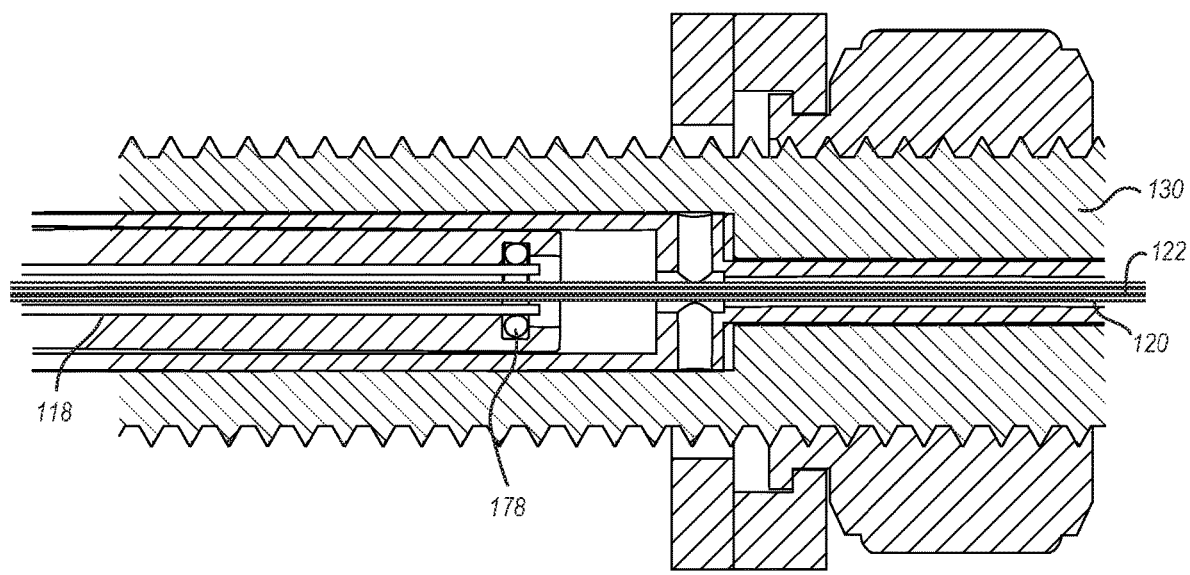
FIG. 6 illustrates a cross-section of a portion of the delivery system where a flushing fluid or gas can be introduced into the delivery catheter of the delivery member of FIG. 1.

Additional components of the delivery member 104 can likewise be flushed. For instance, FIG. 6 illustrates the proximal end of the delivery catheter 118 sealed against the interior of the handle assembly 102 via an O-ring 178. Flushing fluid or gas introduced to the port 158 discussed above in connection with FIG. 3 may pass between an exterior of the suture catheter 120 and the interior of the handle assembly 102 until it reaches the proximal end of the delivery catheter 118. The pressure of the flushing fluid or gas and the seal between the delivery catheter 118 and the interior of the handle assembly 102 may force the flushing fluid or gas into the space between the delivery catheter 118 and the suture catheter 120. As the flushing fluid or gas passes between the delivery catheter 118 and the suture catheter 120, any air or other impurities disposed therebetween may be flushed out and replaced with the flushing fluid or gas.

While FIG. 6 has been described as using the flushing fluid or gas introduced through the port 158 (see FIG. 3), it will be appreciated that a flushing fluid or gas may be introduced into the handle assembly 102 through one or more additional ports. The one or more additional ports may allow for flushing fluid or gas to be introduced into the handle assembly 102 and flush the lumens or spaces between various components of the delivery member 104. For instance, the handle assembly may include a port adjacent to the proximal end of the delivery catheter 118 and through which a flushing fluid or gas may be introduced into the delivery catheter 118. Similarly the handle assembly 102 may include a port adjacent to the proximal end of the steering catheter 114 and through which a flushing fluid or gas may be introduced into the steering catheter 114 and/or the lumens 126 thereof. Alternatively, the components of the delivery member 104, and particularly the proximal ends thereof, may be arranged within the handle assembly 102 such that flushing fluid or gas introduced through the port 158 can pass through one or more of the components of the delivery member 104.

Returning to FIG. 1, each of the valves (148, 152) or ports (e.g., port 150 and port 158) through which a flushing fluid or gas is introduced into the delivery system 100 can be connected to a flushing fluid or gas delivery device 180, such as a CO2MMANDER or other device or system that provides a source of a flushing fluid or gas (e.g., $CO_2$). In some embodiments, such as that illustrated in FIG. 1, the delivery device 180 and the delivery system 100 are connected via a plurality of tubes 182 and a manifold 184. Employing a manifold 184 can allow for selective flushing of all or portions of the delivery member 104. For instance, to flush all of the components of the delivery member 104, all of the manifold valves may be opened and flushing fluid or gas may be delivered to all of the valves and ports of the delivery device 100. In contrast, if only a portion of the delivering member 104 is to be flushed, one or more of the valves of the manifold 184 can be closed such that flushing fluid or gas is delivered only to the desired portions of the delivery member 104.

In some embodiments, the flushing can be automated. For instance, a controller 186 can control the opening and closing of the valves of the manifold 184. As noted above, the flushing of the various components of the delivery member 104 can be done simultaneously or individually. The controller 186 can control the valves of the manifold 184 to enable the desired flushing. In some embodiments, a sensor can detect pressure changes within the various tubes 182, indicating that a sufficient flush has been achieved. In addition or as an alternative to a pressure sensor, a flow sensor can be used to indicate when enough volume has been flushed through the delivery member 104 or specific components thereof. In the illustrated embodiment the controller 186 is shown as part of the manifold 184. In other embodiments, the controller may be part of the delivery device 180 or may be a standalone unit. In any event, after successful flushing, the tubes 182 can be disconnected from the handle assembly and the valves or ports can be closed using a 1 or 2 way stopcock.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for sealing and flushing a delivery member, the method comprising:
   sealing one or more lumens of the delivery member including sealing a suture lumen of a suture catheter that is configured to receive a suture that connects a handle assembly of the delivery member to an interventional device at a distal end of the delivery member, a guidewire tube having one of the one or more lumens and the suture passing through a gasket assembly that closes a flush block connected to a suture catheter holder; and
   flushing a fluid from the one or more lumens.

2. The method of claim 1, further comprising sealing the delivery member in a container and filling the container with $CO_2$.

3. The method of claim 1, wherein sealing the one or more lumens comprises sealing each of the one or more lumens with a flush port.

4. The method of claim 3, wherein following the flushing of the fluid from the one or more lumens comprises closing the flush port to retain a flushing fluid or gas within the one or more lumens.

5. The method of claim 4, further comprising sealing the delivery member in a container.

6. A method for sealing and flushing a delivery member, the method comprising:
   sealing a guide wire lumen of a guidewire tube;
   sealing at least one suture lumen of a suture catheter that is received by a handle assembly, the suture catheter receives the guidewire tube having the guide wire lumen, the at least one suture lumen receiving a suture that connects the handle assembly to an interventional device at a distal end of the delivery member, the guidewire tube and the suture passing through a gasket assembly that closes a flush block connected to the suture catheter holder;
   sealing a delivery catheter disposed about both the suture catheter and the guidewire tube having the guide wire lumen;
   sealing an outer sheath disposed about the delivery catheter; and
   flushing a fluid from the guide wire lumen, the at least one suture lumen, a lumen associated with the delivery catheter, and a lumen of the outer sheath.

7. The method of claim 6, wherein the flushing of the fluid comprises flushing using $CO_2$.

8. The method of claim 6, wherein the flushing of the fluid comprises flushing using a saline solution.

9. The method of claim 6, further comprising connecting a port to at least one of the guide wire lumen, the at least one suture lumen, the lumen associated with the delivery catheter, and the lumen of the outer sheath.

10. The method of claim 6, further comprising sealing the delivery member in a container and filling the container with $CO_2$.

11. The method of claim 6, wherein the sealing at least one of the guide wire lumen, the at least one suture lumen, the lumen associated with the delivery catheter, and the lumen of the outer sheath comprises sealing each with one or more flush ports or valves.

12. The method of claim 11, wherein following the step of flushing the fluid from the at least one of the guide wire lumen, the at least one suture lumen, the lumen associated with the delivery catheter, and the lumen of the outer sheath, the method further comprises closing the one or more flush ports or valves to retain a flushing fluid or gas within the at least one of the guide wire lumen, the at least one suture lumen, the lumen associated with the delivery catheter, and the lumen of the outer sheath.

13. The method of claim 12, further comprising sealing the delivery catheter in a container.

* * * * *